US009720005B2

(12) United States Patent
McConnell et al.

(10) Patent No.: US 9,720,005 B2
(45) Date of Patent: Aug. 1, 2017

(54) IMMUNOASSAY FOR COMPOUNDS OF THE NBOME FAMILY

(71) Applicant: Randox Laboratories Limited, Crumlin Antrim (GB)

(72) Inventors: Ivan Robert McConnell, Ardmore Crumlin (GB); Elouard Benchikh, Crumlin (GB); Peter Fitzgerald, Crumlin (GB); Andrew Philip Lowry, Ardmore Crumlin (GB)

(73) Assignee: Randox Laboratories Limited, Crumlin Antrim (GB)

( * ) Notice: Subject to any disclaimer, the term of this patent is extended or adjusted under 35 U.S.C. 154(b) by 0 days.

(21) Appl. No.: 14/723,724

(22) Filed: May 28, 2015

(65) Prior Publication Data
US 2015/0346226 A1    Dec. 3, 2015

(30) Foreign Application Priority Data
May 29, 2014 (GB) .................................. 1409516.0

(51) Int. Cl.
*G01N 33/94* (2006.01)
*C07K 16/44* (2006.01)

(52) U.S. Cl.
CPC ............ *G01N 33/94* (2013.01); *C07K 16/44* (2013.01); *G01N 33/946* (2013.01); *C07K 2317/30* (2013.01); *C07K 2317/33* (2013.01); *G01N 2430/00* (2013.01)

(58) Field of Classification Search
CPC .. G01N 33/946; G01N 33/94; G01N 2430/00; C07K 16/44; C07K 2317/33; C07K 2317/30
See application file for complete search history.

(56) References Cited

U.S. PATENT DOCUMENTS

| 3,996,344 | A | 12/1976 | Gross |
| 4,016,146 | A | 4/1977 | Soares |
| 4,041,076 | A | 8/1977 | Avenia et al. |
| 5,478,741 | A * | 12/1995 | Maret ................. C07K 16/205 435/34 |
| 2003/0170728 | A1 | 9/2003 | McConnell et al. |
| 2004/0077021 | A1 | 4/2004 | Hui et al. |
| 2004/0121400 | A1 | 6/2004 | McConnell et al. |
| 2015/0038366 | A1 | 2/2015 | Benchikh et al. |

FOREIGN PATENT DOCUMENTS

| EP | 0399184 B1 | 9/1995 |
| EP | 2835648 A1 | 2/2015 |

OTHER PUBLICATIONS

Fujiwara et al. Enzyme immunoassay for the quantification of mitomycin C using b-galactosidase as a label. Cancer Research 1982, vol. 42, pp. 1487-1491.*

(Continued)

*Primary Examiner* — Shafiqul Haq
(74) *Attorney, Agent, or Firm* — McKee, Voorhees & Sease, PLC

(57) ABSTRACT

An immunoassay method for detecting and determining 'NBOMe' family designer drugs is described. Also described are components for use in implementing the method, namely, antibodies, detection agents, solid state devices and kits as well as immunogens used to raise the antibodies.

10 Claims, 5 Drawing Sheets

(56) References Cited

OTHER PUBLICATIONS

Nolli et al. Antibiotics agaisnt the antibiotics: an overview. Ann. 1st. Super. Sanita 1991, vol. 27, No. 1, pp. 149-154.*
Poklis et al. High-performance liquid chromatography with tandem mass spectrometry of the determination of nine hallucinogenic 25-NBOMe designer drugs in urine specimens. J. Analytical Toxicology 2014, vol. 38, pp. 113-121.*
Goodrow et al. Strategies for immunoassay hapten design. Immunoanalysis of Agrochemicals; ACS symposium Series, American Chemical Society: Washington, DC, 1995, pp. 119-139.*
Blaazer, Antoni R. et al., "Structure-Activity Relationships of Phenylalkylamines as Agonist Ligands for 5-HT2A Receptors", ChemMedChem 2008, 3, 1299-1309.
Fitzgerald, Stephen P. et al., "Development of a High-Throughput Automated Analyzer Using Biochip Array Technology", Clinical Chemistry 51:7, 1165-1176 (2005).
Hill, Simon L. et al., "Severe clinical toxicity associated with analytically confirmed recreational use of 251-NBOMe: case series" Clinical Toxicology (2013), 51, 487-492.
Poklis, Justin I. et al., "High-Performance Liquid Chromatography with Tandem Mass Spectrometry for the Determination of Nine Hallucinogenic 25-NB0Me Designer Drugs in Urine Specimens" Journal of Analytical Toxicology, 2014:38-113-121.
UK Intellectual Property Office, "Search Report" issued on behalf of international application No. GB1409516.0, 5 pages, mailed Feb. 9, 2015.
Kim, Yoo Jung, et al., "Synthesis of haptens for immunoassay of organophosphorus pesticides and effect of heterology in hapten spacer arm length on immunoassay sensitivity", Analytica chimica Acta, 475 (2003) 85-96.
Riceberg, Louis J., et al. "Radioimmunoassays of 3,4,5-Trimethoxyphenethylaminie (Mescaline) and 2,5-Dimethoxy-4-Methylphenyl-isopropylamine (DOM)", Analytical Biochemistry (1974) 60: pp. 551-559.
Peterson, Eric C., et al. "Using Hapten Design to Discover Therapeutic Monoclonal Antibodies for Treating Methamphetamine Abuse" Journal of Pharmacology and Experimental Therapeutics (2007) vol. 322, No. 1, 10 pages.
Petrie, M., et al. "Cross-reactivity studies and predictive modeling of "Bath Salts" and other amphetamine-type stimulants with amphetamine screening immunoassays" Clinical Toxicology (2013) 51: pp. 83-91.
Poklis, Justin L., et al. "High-Performance Liquid Chromatography with Tandem Mass Spectrometry for the Determination of Nine Hallucinogenic 25-NBOMe Designer Drugs in Urine Specimens" Journal of Analytical Toxicology (2014) 38: pp. 113-121.
Petrie, E, et al. "Supplementary Material" for "Cross-Reactivity Studies and Predictive Modeling of "Bath Salts" and Other Amphetamine-Type Stimulants with Amphetamine Screening Immunoassays", Clinical Toxicology (2013) 51: pp. 83-91.
RANDOX Toxicology, Brochure for DOx Series ELISA Kit, 2 pages.
Swortwood, Madeleline, J., et al. "Cross-Reactivity of Designer Drugs, including Cathinone Derivatives, in Commercial Enzyme-Linked Immunosorbent Assays" Drug Testing and Analysis (2013), 12 pages.
Vorce, Shawn P., et al. "Dimethylamylamine" A Drug Causing Positive Immunoassay Results for Amphetamines, Journal of Toxicology (2011) vol. 35, 5 pages.
Non-Final Office Action mailed Oct. 17, 2016 U.S. Appl. No. 14/451,964, 19 pages.
Randox Laboratories, Ltd., Application No. 15168829.8, "Extended European Search Report" mailed Sep. 10, 2015, 7 pages.

* cited by examiner

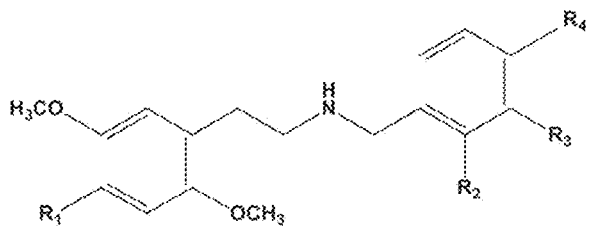

| COMPOUND | R₁ | R₂ | R₃ | R₄ |
|---|---|---|---|---|
| 25I-NBOMe (1) | I | OCH₃ | H | H |
| 25I-NB3OMe (2) | I | H | OCH₃ | H |
| 25I-NB4OMe (3) | I | H | H | OCH₃ |
| 25I-NBOH (4) | I | OH | H | H |
| 25I-NBF (5) | I | F | H | H |
| 25I-NBMD (6) | I | O    -CH₂- | O | H |
| 25B-NBOMe (7) | Br | OCH₃ | H | H |
| 25B-NB3OMe (8) | Br | H | OCH₃ | H |
| 25B-NB4OMe (9) | Br | H | H | OCH₃ |
| 25B-NBOH (10) | Br | OH | H | H |
| 25B-NBF (11) | Br | F | H | H |
| 25B-NBMD (12) | Br | O    -CH₂- | O | H |
| 25C-NBOMe (13) | Cl | OCH₃ | H | H |
| 25C-NB3OMe (14) | Cl | H | OCH₃ | H |
| 25C-NB4OMe (15) | Cl | H | H | OCH₃ |
| 25C-NBOH (16) | Cl | OH | H | H |
| 25C-NBF (17) | Cl | F | H | H |
| 25C-NBMD (18) | Cl | O -CH₂- | O | H |
| 25F-NBOMe (19) | F | OCH₃ | H | H |
| 25F-NB3OMe (20) | F | H | OCH₃ | H |
| 25F-NB4OMe (21) | F | H | H | OCH₃ |
| 25F-NBOH (22) | F | OH | H | H |
| 25F-NBF (23) | F | F | H | H |
| 25F-NBMD (24) | F | O    -CH₂- | O | H |
| 25D-NBOMe (25) | CH₃ | OCH₃ | H | H |
| 25D-NB3OMe (26) | CH₃ | H | OCH₃ | H |
| 25D-NB4OMe (27) | CH₃ | H | H | OCH₃ |
| 25D-NBOH (28) | CH₃ | OH | H | H |
| 25D-NBF (29) | CH₃ | F | H | H |
| 25D-NBMD (30) | CH₃ | O    -CH₂- | O | H |
| 25E-NBOMe (31) | CH₃CH₂ | OCH3 | H | H |
| 25E-NB3OMe (32) | CH₃CH₂ | H | OCH₃ | H |
| 25E-NB4OMe (33) | CH₃CH₂ | H | H | OCH₃ |
| 25E-NBOH (34) | CH₃CH₂ | OH | H | H |
| 25E-NBF (35) | CH₃CH₂ | F | H | H |
| 25E-NBMD (36) | CH₃CH₂ | O    -CH₂- | O | H |
| 25P-NBOMe (37) | CH₂CH₂CH₃ | OCH₃ | H | H |
| 25P-NB3OMe (38) | CH₂CH₂CH₃ | H | OCH₃ | H |
| 25P-NB4OMe (39) | CH₂CH₂CH₃ | H | H | OCH₃ |
| 25P-NBOH (40) | CH₂CH₂CH₃ | OH | H | H |
| 25P-NBF (41) | CH₂CH₂CH₃ | F | H | H |
| 25P-NBMD (42) | CH₂CH₂CH₃ | O    -CH₂- | O | H |

Figure 1A

| | | | | |
|---|---|---|---|---|
| 25T-NBOMe (43) | CH₃S | OCH₃ | H | H |
| 25T-NB3OMe (44) | CH₃S | H | OCH₃ | H |
| 25T-NB4OMe (45) | CH₃S | H | H | OCH₃ |
| 25T-NBOH (46) | CH₃S | OH | H | H |
| 25T-NBF (47) | CH₃S | F | H | H |
| 25T-NBMD (48) | CH₃S | O       -CH₂- | O | H |
| 25T2-NBOMe (49) | CH₃CH₂S | OCH₃ | H | H |
| 25T2-NB3OMe (50) | CH₃CH₂S | H | OCH₃ | H |
| 25T2-NB4OMe (51) | CH₃CH₂S | H | H | OCH₃ |
| 25T2-NBOH (52) | CH₃CH₂S | OH | H | H |
| 25T2-NBF (53) | CH₃CH₂S | F | H | H |
| 25T2-NBMD (54) | CH₃CH₂S | O       -CH₂- | O | H |
| 25T7-NBOMe (55) | CH₃CH₂CH₂S | OCH3 | H | H |
| 25T7-NB3OMe (56) | CH₃CH₂CH₂S | H | OCH3 | H |
| 25T7-NB4OMe (57) | CH₃CH₂CH₂S | H | H | OCH3 |
| 25T7-NBOH (58) | CH₃CH₂CH₂S | OH | H | H |
| 25T7-NBF (59) | CH₃CH₂CH₂S | F | H | H |
| 25T7-NBMD (60) | CH₃CH₂CH₂S | O       -CH₂- | O | H |
| 25TFM-NBOMe (61) | CF₃ | OCH₃ | H | H |
| 25TFM-NB3OMe (62) | CF₃ | H | OCH₃ | H |
| 25TFM-NB4OMe (63) | CF₃ | H | H | OCH₃ |
| 25TFM-NBOH (64) | CF₃ | OH | H | H |
| 25TFM-NBF (65) | CF₃ | F | H | H |
| 25TFM-NBMD (66) | CF₃ | O       -CH₂- | O | H |
| 25N-NBOMe (67) | NO₂ | OCH3 | H | H |
| 25N-NB3OMe (68) | NO₂ | H | OCH₃ | H |
| 25N-NB4OMe (69) | NO₂ | H | H | OCH₃ |
| 25N-NBOH (70) | NO₂ | OH | H | H |
| 25N-NBF (71) | NO₂ | F | H | H |
| 25N-NBMD (72) | NO₂ | O       -CH₂- | O | H |
| Mescaline-NBOMe (73) | OCH₃ | OCH₃ | H | H |
| 25H-NBOMe (74) | H | OCH₃ | H | H |
| 25H-NB3OMe (75) | H | H | OCH₃ | H |
| 25H-NB4OMe (76) | H | H | H | OCH₃ |
| 25H-NBOH (77) | H | OH | H | H |
| 25H-NBF (78) | H | F | H | H |
| 25H-NBMD (79) | H | O       -CH₂- | O | H |
| 25T4-NBOMe (80) | CH₃CH₃CHS | OCH₃ | H | H |
| 25T4-NB3OMe (81) | CH₃CH₃CHS | H | OCH₃ | H |
| 25T4-NB4OMe (82) | CH₃CH₃CHS | H | H | OCH₃ |
| 25T4-NBOH (83) | CH₃CH₃CHS | OH | H | H |
| 25T4-NBF (84) | CH₃CH₃CHS | F | H | H |
| 25T4-NBMD (85) | CH₃CH₃CHS | O       - CH₂- | O | H |

Figure 1B

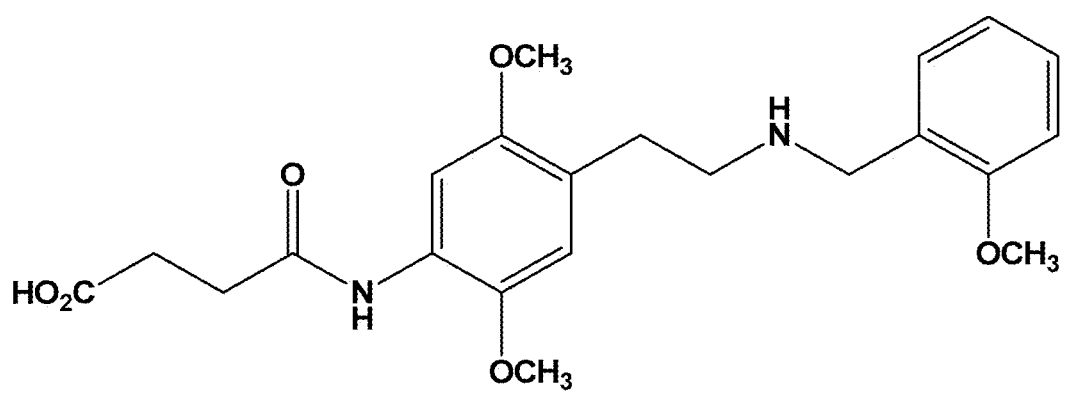
Hapten-2
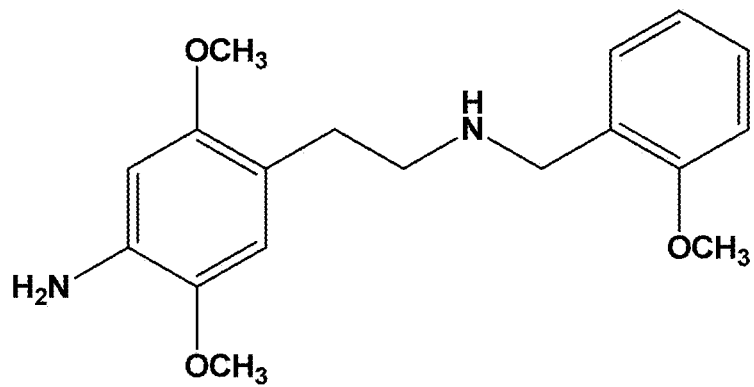
Hapten-1
Figure 2

IMMUNOASSAY FOR COMPOUNDS OF THE NBOME FAMILY

CROSS REFERENCE TO RELATED APPLICATIONS

This application claims priority to UK Application No. 1409516.0 filed May 29, 2014, herein incorporated by reference in its entirety.

BACKGROUND OF THE INVENTION

Phenethylamines can be depicted as:

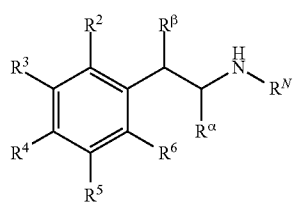

Structure (X)

and the 2C-X compounds are substituted 2,5-dimethoxyphenethylamines in which $R^3$ and $R^6$ are methoxy, and $R^N$, $R^\alpha$ and $R^\beta$ are each hydrogen.

The 'NBOMe' compounds are highly potent hallucinogenic phenethylamine derivatives which have recently been encountered in cases of recreational drug use. Specifically they are 2C-X compounds in which $R^N$ is an optionally substituted benzyl derivative—also known as N-benzyl derivatives of the substituted 2,5-dimethoxyphenethylamine 2C-X compounds. This modification appears to significantly enhance their potency and therefore increases the risk of overdoses by miscalculation of dose. For example, while a dose of 2C-I is around 20 milligrams, the dose of the NBOMe equivalent (25I-NBOMe) is less than one milligram (Blaazer et al. 2008). NBOMe compounds act as potent serotonin agonists particularly at the 5-HT$_{2A}$ receptors which mediate the primary effects of hallucinogenic drugs. Their effects have been compared to lysergic acid diethylamide (LSD) and they are often sold either as 'legal' alternatives to this drug or misleadingly sold as LSD itself. NBOMe compounds are sold as freebase, hydrochlorides or can be complexed to hydroxypropyl beta-cyclodextrin (HPBCD) to increase bioavailability. Like LSD, NBOMe compounds are active at very low doses and therefore are often sold in the form of paper blotters which are administered by placing under the tongue.

Some of the NBOMe compounds most commonly encountered by law enforcement agencies include 25D-NBOMe-2-(2,5-Dimethoxy-4-methylphenyl)-N-[(2-methoxyphenyl)methyl]ethanamine (see FIG. 1A, 1B), 25B-NBOMe-2-(4-Bromo-2,5-dimethoxyphenyl)-N-[(2-methoxyphenyl)methyl]ethanamine (see FIG. 1A, 1B), 25I-NBOMe-2-(4-Iodo-2,5-dimethoxyphenyl)-N-[(2-methoxyphenyl)methyl] ethanamine (see FIG. 1 1A, 1B), 25C-NBOMe-2-(4-Chloro-2,5-dimethoxyphenyl)-N-[(2-methoxyphenyl)methyl]ethanamine (see FIG. 1A, 1B) and 25H-NBOMe-2-(2,5-dimethoxyphenyl)-N-(2-methoxybenzyl)ethanamine (see FIG. 1A, 1B).

The exact pharmacological and toxicological effects of many of these synthetic compounds in humans are unknown and can be unpredictable. The onset of effects is rapid and the duration is generally 2-4 hours but they can last much longer depending of the dose. Side effects may last up to 7 days however there are some reports of side effects persisting for months after use. Clinical features recorded in a case study of 25I-NBOMe use included tachycardia, hypertension, agitation, aggression, visual and auditory hallucinations, seizures, hyperplexia, clonus, elevated white cell count, elevated creatine kinase, metabolic acidosis and acute kidney injury (Hill et al 2013). NBOMe compounds have been associated with a number of deaths.

Many governments around the world have taken steps to illegalise this NBOMe family of novel designer drugs. For example, the UK home office issued a temporary class drug order (TCDO) on 4 Jun. 2013, which took effect on 10 Jun. 2013, prohibiting the production, import and sale of NBOMe compounds. Subsequently all N-Benzyl phenethylamines have been placed on the permanent controlled list and will be class A drugs in the UK from 10 Jun. 2014. Similarly in the United States the DEA made 25B-NBOMe, 25I-NBOMe and 25C-NBOMe schedule I controlled drugs for at least 2 years from 15 Nov. 2013.

Current analytical methods use mass-spectrometry (MS) in conjunction with gas chromatography (GC) or liquid chromatography (LC) (e.g. Poklis et al 2014). A disadvantage of such methods of detection is that they require expensive equipment and highly trained staff. On the other hand, immunoassays are known in the art as relatively cost effective, simplistic and rapid alternatives to MS based analysis. There remains a need for an assay which is not only sensitive to the NBOMe compounds currently found in seized drugs, but that can also detect analogues and derivatives which may make their way onto the market in future so as to enable improvements in the forensic toxicological and clinical analysis of the intake of these ever evolving designer drugs.

SUMMARY OF THE INVENTION

Described herein are the first known immunoassays for the selective detection and determination of the NBOMe sub-family of phenethylamine based designer drugs. The immunoassays are underpinned by novel, sensitive, sub-family-specific antibodies. The invention further describes substrates comprising an antibody that is specific to compounds of the NBOMe sub-family. Also described are novel immunogens and kits incorporating antibodies of the current invention.

REFERENCES

Blaazer, A. R et al. "Structure-activity relationships of phenylalkylamines as agonist ligands for 5-HT2A receptors". ChemMedChem (2008); 3(9), 1299-1309.

FitzGerald, S. P. et al. "Development of a high-throughput automated analyser using Biochip Array Technology". Clin. Chem. (2005); 51(7), 1165-1176.

Hill, S. L et al. "Severe clinical toxicity associated with analytically confirmed recreational use of 25I-NBOMe: case series". Clin. Toxicol. (2013); 51, 487-492.

Immunoassay: A practical guide, by Brian Law, Taylor and Francis Ltd, ISBN 0-203-48349-9.

Poklis, J. L et al. "High-performance liquid chromatography with tandem mass spectrometry for the determination of nine 25-NBOMe designer drugs in urine specimens." J. Anal. Toxicol. (2014); 38, 113-121.

BRIEF DESCRIPTION OF THE DRAWINGS

FIG. 1A, 1B—Structural formulae for compounds belonging to the NBOMe sub-family of phenethylamines (compounds are numbered 1-85 in brackets for reference purposes herein).

FIG. 2—Chemical Structures of haptens 1 and 2.

DETAILED DESCRIPTION OF THE INVENTION

Figure 3:
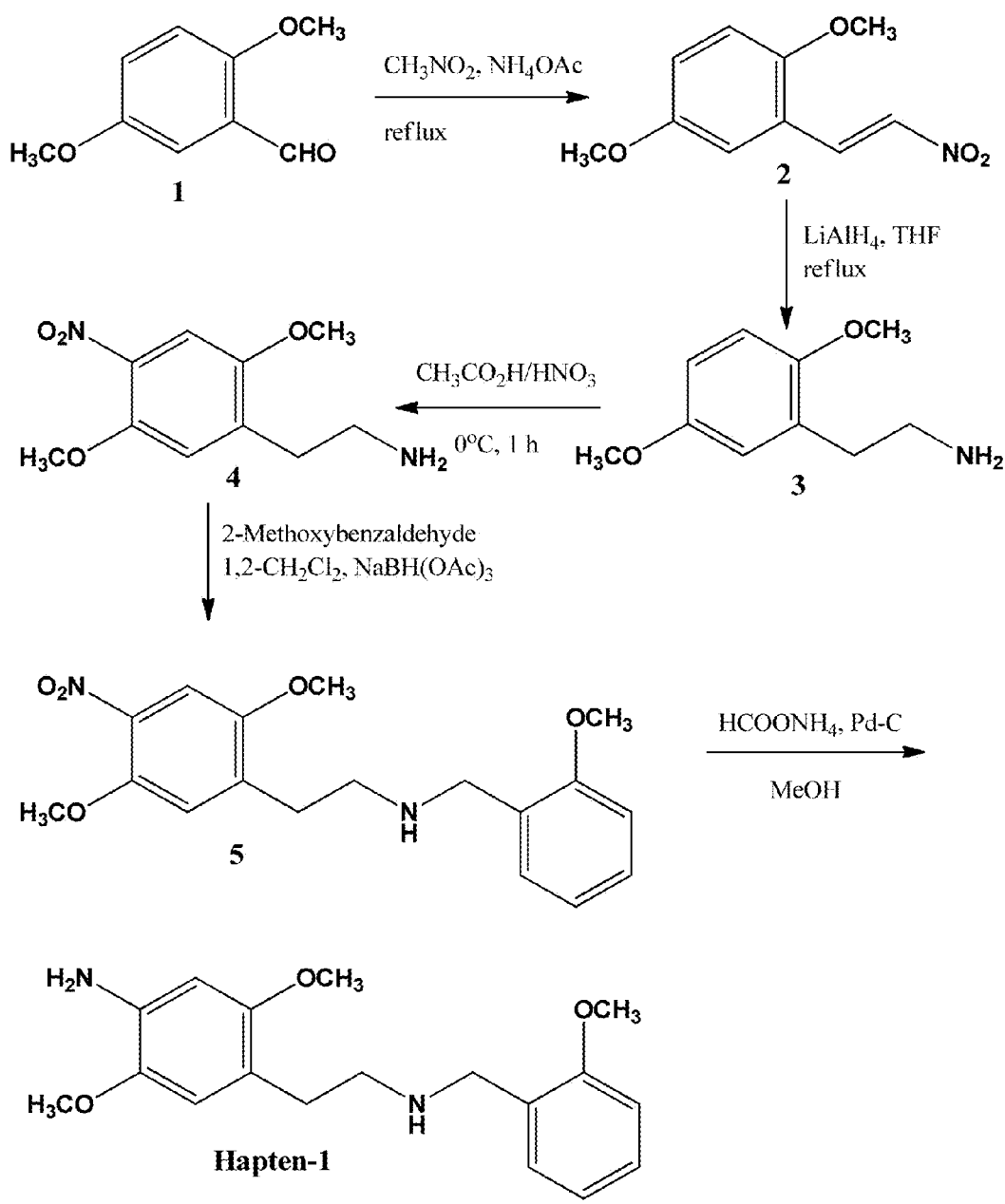
FIG. 3—Chemical Reactions for the synthesis of hapten 1.
Figure 4:
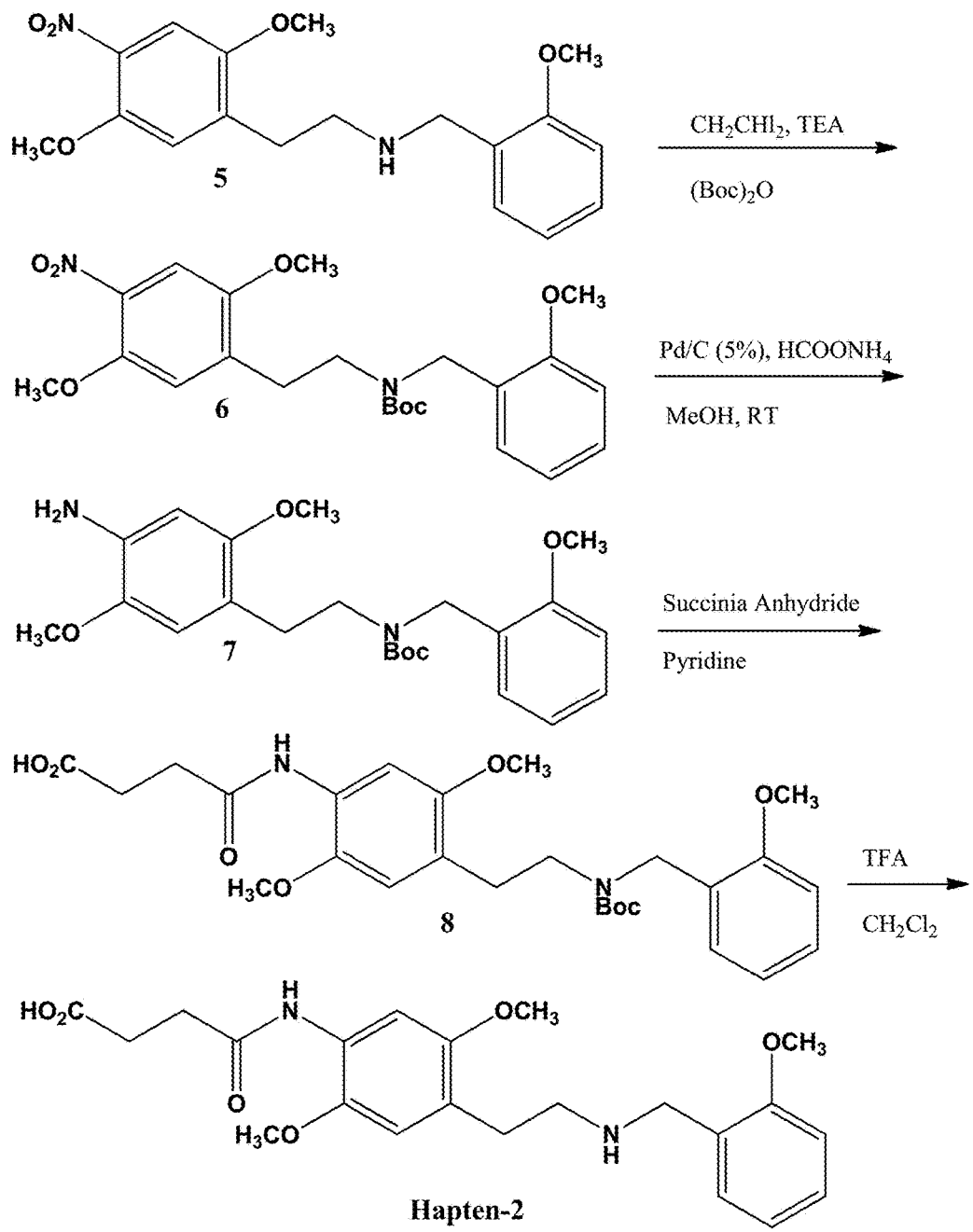
FIG. 4—Chemical Reactions for the synthesis of hapten 2.

Unless otherwise stated, technical terms as used herein are used according to the conventional usage as known to those skilled in the art.

The chemical structures of the "NBOMe" compounds referred to herein are illustrated in FIG. 1A, B. A reference number has been given in brackets next to each compound name for clarity purposes. The suffix "NBOMe" as used herein may also be referred to herein as NB2OMe (25-NB2OMe), the 2 indicating the position of the methoxy group on the $R^N$ of the phenethylamine structure (Structure (X), being the benzyl group.

The invention describes a method of detecting or determining NBOMe compounds in a solution or an in vitro sample of an individual comprising; contacting the sample with one or more detecting agents and one or more antibodies; detecting, or determining the quantity of the one or more detecting agents; and deducing from calibrators the presence of or amount of NBOMe compounds in the sample or solution, the one or more antibodies characterised by having been derived from an immunogen of structure II.

The term "hapten" as used herein describes a pre-immunogenic molecule that stimulates antibody production only when conjugated to a larger carrier molecule. This larger carrier molecule can be referred to as an antigenicity-conferring carrier material (accm). Once the hapten is conjugated to the accm, it forms the immunogen.

The term "immunogen" as used herein, describes an entity that induces an immune response such as production of antibodies or a T-cell response in a host animal.

The accm can be any material that makes all or part of the hapten susceptible to antibody recognition and binding. For example the accm can be a protein, a protein fragment, a synthetic polypeptide or a semi-synthetic polypeptide. Alternatively, the accm comprises synthetic poly(amino acids) having a sufficient number of available amino groups, such as lysine. Further alternatively, the accm is selected from synthetic or natural polymeric materials bearing reactive functional groups. Still further alternatively the accm is selected from carbohydrates, yeasts and polysaccharides. Illustrative examples of useful antigenicity-conferring carrier materials are bovine serum albumin (BSA), egg ovalbumin (OVA), bovine gamma globulin (BGG), bovine thyroglobulin (BTG), keyhole limpet haemocyanin (KLH) etc. Optionally the accm is selected from BTG or BSA.

It will be understood that the haptens of the current invention may be attached to the antigenicity-conferring carrier material (accm) via a cross-linking group or cross-linker. The cross-linking group may be any conventional cross linking group conventionally used in this field. The cross-linking group is ideally a functionalised linking group joining the accm to the hapten. Preferably, the cross-linking group may comprise or consist of a carboxyl, dithiopyridyl, maleimidyl, amino, hydroxyl, thiol and aldehyde moiety. The cross-linking group is well known to the skilled person in immunogen synthesis. In a preferred embodiment of the current invention, glutaraldehyde may be used to join hapten 1 and the accm. Glutaraldehyde reacts with the free amino groups on both the hapten and accm to form a cross-linker between the two. In this manner, the accm is conjugated via a cross-linking group to the nitrogen at position 4 of the dimethoxyphenyl group of hapten 1.

Alternatively, the haptens of the current invention may be directly conjugated or directly coupled to the antigenicity-conferring carrier material (accm) to form the immunogen. In this case, hapten 2 may be directly coupled to the accm via an amide bond, utilising a carbodiimide compound such as N, N-dicyclohexylcarbodiimide (DCC) to facilitate the reaction. These carbodiimides (such as EDC or DCC) facilitate the reaction between the carboxyl group ($CO_2H$ of R) on the hapten and free amino groups on the accm to form amide bonds with no crosslinking groups present between the conjugated molecules. In this manner, direct coupling takes place via amide bond formation. In this manner, the accm is conjugated directly to the carboxy-group of hapten 2.

According to a general aspect of the invention there is provided a hapten having the general formula:

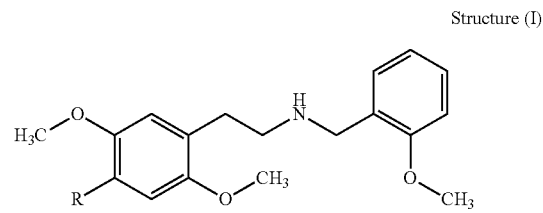

Structure (I)

Wherein R is:

-(A)-(B)$_n$—, where A is O, S or N and B is a $C_{1-6}$ substituted or unsubstituted straight chain alkylene or arylene moiety, n is either 0 or 1 and wherein A is attached to the phenyl ring. When A is N, H supplies any additional valencies.

Optionally, R is a substituted or unsubstituted amino group.

Examples of preferred haptens of the current invention are 25NH2-NBOMe (hapten 1 herein) and N-(2-methoxybenzyl)-2-(2,5-dimethoxy-4-succinamidophenyl)ethylamine (hapten 2 herein). Where the hapten is 25NH2-NBOMe, A is $NH_2$ and n is 0. Where the hapten is N-(2-methoxybenzyl)-2-(2,5-dimethoxy-4-succinamidophenyl)ethylamine, A is NH and B is —C(O)—$CH_2$—$CH_2$—$CO_2H$, n is 1.

According to a second general aspect of the invention, there is provided an immunogen having the general formula:

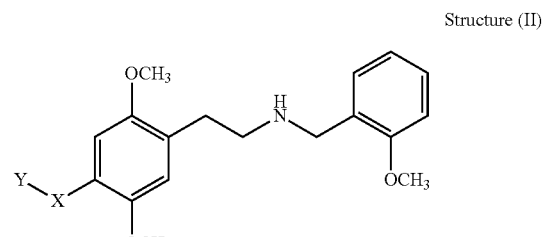

Structure (II)

Wherein X is a cross-linking group and Y is an antigenicity-conferring carrier material.

Optionally, X is -(A)-(B)$_n$—, where A is O, S or N and B is a C$_{1-6}$ substituted or unsubstituted straight chain alkylene or arylene moiety and n is either 0 or 1 and A is attached to the phenyl ring.

Optionally, X is -(A)-(B)$_n$—, where A is O, S or N and B is a C$_{1-6}$ substituted or unsubstituted straight chain alkylene terminating, before conjugation with the antigenicity-conferring carrier material, with a terminal reactive group and n is either 0 or 1.

When A is N, H supplies any additional valencies.

Further optionally, X is -(A)-(B)$_n$—, where A is NH and B is a C$_{1-6}$ substituted or unsubstituted straight chain alkylene terminating, before conjugation with the antigenicity-conferring carrier material, with a terminal reactive group and n is either 0 or 1. Preferably, in any of these embodiments, n is 0 and, when n is 0, A is optionally NH$_2$. In any of these embodiments, A is attached to the phenyl ring. The substituents of the alkylene chain can either be incorporated off, within or at the end of the chain. Usually the substituents will be functional groups at the end of the chain (terminal reactive groups) which have participated in chemical bonding in order to form a link between the substituted phenethylamine structure and the carrier material. The conjugation to Y can be facilitated by, for example, the presence of a terminal reactive group selected from a carboxylic acid or an ester thereof, an aldehyde, an amino group, a maleimide, a halocarboxylic acid or an ester thereof, a dithiopyridyl moiety, a vinylsulphone moiety, a thiocarboxylic acid or an ester thereof.

An example of a preferred immunogen of the current invention is 25NH2-NBOMe conjugated to BTG or BSA, optionally BTG. This is accomplished using gluteraldehyde followed by a reduction of the resulting Schiff base by sodium borohydride. The preparation of these example immunogens is given in Examples 10 and 11—this is conjugation using a diketone such as glutaraldehyde. In another example, A is N and B is, before conjugation to Y, —C(O)—CH$_2$—CH$_2$—CO$_2$H, n is 1 and Y is BTG or BSA—this is direct conjugation.

A further aspect of the current invention is an antibody raised to an immunogen described above. The term "antibody" as used herein refers to an immunoglobulin or immunoglobulin-like molecule. In a preferred embodiment, the antibodies are polyclonal antibodies. However, the skilled person will understand that any type of immunoglobulin molecule or fragment thereof can be used, for example monoclonal antibodies, Fab fragments, scFv fragments and any other antigen binding fragments all of which fall within the scope of the current invention. The polyclonal antibodies may be produced by any method as known to those skilled in the art. Any suitable host animal may be used in the immunisation process, preferably a mammalian animal for example, but not limited to, sheep, rabbit, mouse, guinea pig or horse. In addition, the antibodies may be in the form of polyclonal antisera.

When used in reference to an antibody, the word 'specific' or 'specificity' in the context of the current invention refers to the analyte or analytes that are preferably bound by the antibody, as gauged by a suitable metric such as the cross-reactivity. For purposes of comparison, one analyte with high cross-reactivity is generally given a value of 100%, with all other analytes accorded a value relative to this. Herein, 25I-NBOMe.HCl is given a value of 100%.

In addition, as is known by one skilled in the art, for cross-reactivity to be of practical use, the analyte specific antibody must display a high sensitivity as measured by a suitable metric such as the IC$_{50}$. The IC$_{50}$ is a commonly used indicator of antibody sensitivity for immunoassays.

Optionally, the antibody of the invention is capable of binding to at least one epitope from the group comprising the molecules 25I-NBOMe, 25P-NBOMe, Mescaline-NBOMe, 25B-NBOMe, 25D-NBOMe, 25E-NBOMe, 25H-NBOMe, 25N-NBOMe, 25T2-NBOMe, 25T4-NBOMe and 25T7-NBOMe. (Compounds 1, 37, 73, 7, 25, 31, 74, 67, 49, 80 and 55 of FIG. 1A, B). The term 'able to bind to' or "capable of binding" as used herein means that, under standard immunoassay conditions, for example as described in 'Immunoassay: A practical guide' by Brian Law, Taylor and Francis Ltd (ISBN 0-203-48349-9), the antibodies will bind to said molecules.

In a further embodiment, the antibody is additionally capable of binding to one or more molecules selected from the group 25I-NBOH, 25I-NBF, 25I-NBMD, 25B-NBOH, 25B-NBF, 25B-NBMD, 25C-NBOMe, 25C-NBOH, 25C-NBF, 25C-NBMD, 25F-NBOMe, 25F-NBOH, 25F-NBF, 25F-NBMD, 25D-NBOH, 25D-NBF, 25D-NBMD, 25E-NBOH, 25E-NBF, 25E-NBMD, 25P-NBOH, 25P-NBF, 25P-NBMD, 25T-NBOMe, 25T-NBOH, 25T-NBF, 25T-NBMD, 25T2-NBOH, 25T2-NBF, 25T2-NBMD, 25T4-NBOH, 25T4-NBF, 25T4NBMD, 25T7-NBOH, 25T7-NBF, 25T7-NBMD, 25TFM-NBOMe, 25TFM-NBOH, 25TFM-NBF, 25TFM-NBMD, 25N-NBF, 25N-NBMD, 25H-NBOMe, 25H-NBOH, 25H-NBF, 25H-NBMD, 25N-NBOH and 25NH2-NBOH.

Further optionally, the antibody is capable of binding to one or more of the molecules selected from the group 25I-NB3OMe, 25I-NB4OMe, 25B-NB3OMe, 25B-NB4OMe, 25C-NB3OMe, 25C-NB4OMe, 25F-NB3OMe, 25F-NB4OMe, 25D-NB3OMe, 25D-NB4OMe, 25E-NB3OMe, 25E-NB4OMe, 25P-NB3OMe, 25P-NB4OMe, 25T-NB3OMe, 25T-NB4OMe, 25T2-NB3OMe, 25T2-NB4OMe, 25T4-NB3OMe, 25T4-NB4OMe, 25T7-NB3OMe, 25T7-NB4OMe, 25TFM-NB3OMe, 25TFM-NB4OMe, 25N-NB3OMe, 25N-NB4OMe, 25H-NB3OMe and 25H-NB4OMe.

We have advantageously found that the antibody of the invention is specific for at least one epitope of at least 25I-NBOMe, 25P-NBOMe, Mescaline-NBOMe, 25B-NBOMe, 25D-NBOMe, 25E-NBOMe, 25H-NBOMe, 25N-NBOMe, 25T2-NBOMe, 25T4-NBOMe and 25T7-NBOMe.

Optionally, the antibody has 100% cross-reactivity to 25I-NBOMe and greater than 10%, optionally greater than 15%, cross-reactivity to the group comprising of, but not limited to, 25N-NBOH and 25NH2-NBOH, optionally when measured according to Example 13.

Optionally or additionally, the antibody has 100% cross-reactivity to 25I-NBOMe and less than 35%, optionally less than 30%, cross-reactivity to either one or both of 25N-NBOH and 25NH2-NBOH, optionally when measured according to Example 13.

Alternatively, the antibody has 100% cross-reactivity to 25I-NBOMe and greater than 75%, optionally greater than 100% cross-reactivity to 25P-NBOMe, Mescaline-NBOMe, 25B-NBOMe, 25D-NBOMe, 25E-NBOMe, 25H-NBOMe, 25N-NBOMe, 25T2-NBOMe, 25T4-NBOMe and 25T7-NBOMe. 'Greater than 75% or 100% cross-reactivity' in this case refers to the cross-reactivity to said compound relative to the 100% cross-reactivity to 25I-NBOMe. Alternatively or additionally, the antibody has 100% cross-reactivity to 25I-NBOMe and less than 200% cross-reactivity to 25P-NBOMe, Mescaline-NBOMe, 25B-NBOMe, 25D-NBOMe, 25E-NBOMe, 25H-NBOMe, 25N-NBOMe, 25T2-NBOMe, 25T4-NBOMe and 25T7-NBOMe. 'Less than 200% cross-reactivity' in this case refers to the cross-reactivity to said compound relative to the 100% cross-reactivity to 25I-NBOMe.

Still optionally, the antibody has 100% cross-reactivity to 25I-NBOMe, and greater than 75\%, optionally greater than 100%, cross-reactivity for 25P-NBOMe, Mescaline-NBOMe, 25B-NBOMe, 25D-NBOMe, 25E-NBOMe, 25H-NBOMe, 25N-NBOMe, 25T2-NBOMe, 25T4-NBOMe and 25T7-NBOMe, and greater than 10% cross-reactivity to the group comprising of, but not limited to, 25N-NBOH and 25NH2-NBOH. Alternatively or additionally, the antibody has 100% cross-reactivity to 25I-NBOMe, and less than 200% cross-reactivity for 25P-NBOMe, Mescaline-NBOMe, 25B-NBOMe, 25D-NBOMe, 25E-NBOMe, 25H-NBOMe, 25N-NBOMe, 25T2-NBOMe, 25T4-NBOMe and 25T7-NBOMe, and less than 35% cross-reactivity to either one or both of 25N-NBOH and 25NH2-NBOH.

Additionally or alternatively, the antibody may be characterised in that it shows no significant binding, preferably at 100 ng/ml of cross-reactant as defined in the examples, to 2C-B, 2C-I, 2C-E or DOB. As used herein, the term 'no significant binding' can be understood to mean any low cross-reactivity which would not compromise the assay. Optionally, this corresponds to a cross-reactivity of less than 5% relative to the analyte which has been given a value of 100% cross reactivity (25I-NBOMe herein), optionally when measured according to Example 13. More preferably, the cross-reactivity is less than 4% or 3% and even more preferably the cross-reactivity is less than 2% or 1% relative to the analyte which has been given a value of 100% cross reactivity for the assay, optionally when measured according to Example 13.

Additionally or alternatively, the antibody of the current invention may be characterised by its high sensitivity. Preferably, it has an $IC_{50}$ of <about 5 ng/ml, preferably <about 1 ng/ml, more preferably <about 0.5 ng/ml and even more preferably <about 0.2 ng/ml for one or more NBOMe compounds selected from, but not limited to, 25I-NBOMe, 25P-NBOMe, Mescaline-NBOMe, 25B-NBOMe, 25D-NBOMe, 25E-NBOMe and 25H-NBOMe, optionally when measured according to Example 13. Preferably, it has an $IC_{50}$ in the range of 0.075 to 0.175 mg/ml for one or more NBOMe compounds selected from, but not limited to, 25I-NBOMe, 25P-NBOMe, Mescaline-NBOMe, 25B-NBOMe, 25D-NBOMe, 25E-NBOMe and 25H-NBOMe, optionally when measured according to Example 13. In a preferred embodiment, the antibody has an $IC_{50}$ selected from one or more of at least about 0.164 ng/ml for 25I-NBOMe; at least about 0.147 ng/ml for 25P-NBOMe; at least about 0.138 ng/ml for 25B-NBOMe; at least about 0.1 ng/ml for mescaline-NBOMe; at least about 0.104 ng/ml for 25D-NBOMe; at least about 0.13 ng/ml for 25E-NBOMe; and at least about 0.096 ng/ml for 25H-NBOMe, optionally when measured according to Example 13. The use of the word 'about' accounts for the expected minor variations in the measured $IC_{50}$ value which may arise during scientific analyses by different individuals when effecting the assay or from slight differences in assay equipment and reagents.

A further aspect of the invention is an immunoassay method of detecting or determining NBOMe compounds or derivatives thereof in an in vitro sample from an individual or in a solution derived from a substance suspected to contain such compounds, the method comprising contacting the sample or solution with at least one detecting agent and at least one antibody of the invention; detecting or determining the detecting agent(s); and deducing from a calibration curve the presence of, or amount of NBOMe compounds in the sample or solution.

For the purposes of the invention, the sample to be used for in vitro analysis can be any sample from which an 'NBOMe' compound can be detected for example hair or a peripheral biological fluid but is preferably whole blood, serum, plasma, or urine. The sample may also be a solution which is suspected of containing a drug.

'Detecting' as referred to herein means qualitatively analysing for the presence or absence of a substance, while 'determining' means quantitatively analysing for the amount of a substance. The detecting agent is a small molecule (generally of similar structure to a molecule to be detected), conjugated to a labelling agent that is able to bind to one of the antibodies of the invention. Alternative names for the detecting agent are the conjugate or tracer. The labelling agent is selected from an enzyme, a luminescent substance, a radioactive substance, or a mixture thereof. Preferably, the labelling agent is an enzyme, preferably a peroxidase, most preferably horseradish peroxidase (HRP). Alternatively, or additionally, the luminescent substance may be a bioluminescent, chemiluminescent or fluorescent material. Preferably, for the immunoassay method of the invention, the detecting agent is based on a compound with a substituted-phenethylamine substructure conjugated to an enzyme or fluorescent molecule.

Preferably, the conjugate or detecting agent used in the immunoassays of the current invention is of the structure:

Structure (III)

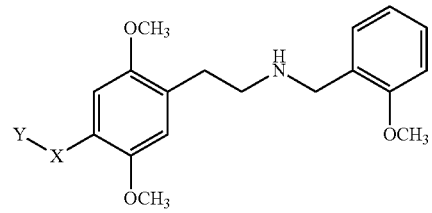

In which X is a cross-linking group and Y is a labelling agent which is detectable.

Preferably, the cross-linking group X is -(A)-(B)$_{n1}$—, where A, attached to position 4 of the phenyl ring, is O, S or N and B is a $C_{1-10}$, preferably $C_{1-6}$, substituted or unsubstituted straight chain alkylene or arylene moiety and n1 is either 0 or 1. The substituents of the alkylene chain can either be incorporated off, within or at the end of the chain.

When A is N, H supplies any additional valencies.

Optionally, X is -(A)-(B)$_{n1}$—, where A is O, S or N and B is a $C_{1-6}$ substituted or unsubstituted straight chain alkylene terminating, before conjugation with the labelling agent, with a terminal reactive group and $n_1$ is either 0 or 1. Further optionally, X is -(A)-(B)$_{n1}$—, where A is NH and B is a $C_{1-6}$ substituted or unsubstituted straight chain alkylene terminating, before conjugation with the labelling agent, with a terminal reactive group and $n_1$ is either 0 or 1. In any of these embodiments, $n_1$ is preferably 1. Usually the substituents will be functional groups at the end of the chain (terminal reactive groups) which have participated in chemical bonding in order to form a link between the substituted phenethylamine structure and the labelling agent. The conjugation to Y can be facilitated by, for example, the presence of a terminal reactive group selected from a carboxylic acid or an ester thereof, an aldehyde, an amino group, a maleimide, a halocarboxylic acid or an ester thereof, a dithiopyridyl moiety, a vinylsulphone moiety, a thiocarboxylic acid or an ester thereof.

Preferably, the labelling agent is horseradish peroxidase (HRP). Other conventional labelling agents may be used selected from an enzyme, such as peroxidase, a luminescent substance, a radioactive substance or a mixture thereof.

An example of a preferred conjugate or detecting agent of the current invention is N-(2-methoxybenzyl)-2-(2,5-dimethoxy-4-succinamidophenyl)ethylamine (Hapten 2) coupled to HRP. In this example A is NH and B, before conjugation to Y, is —C(O)—CH$_2$—CH$_2$—CO$_2$H, $n_1$ is 1 and Y is HRP. The preparation of this example conjugate is given in Example 12.

The invention further describes a substrate with which the antibodies of the invention engage. The antibodies can engage with the substrate by, for example, passive adsorption or can be chemically bonded to the substrate attached by way of, for example, covalent bonds. Such covalent bonding generally requires the initial introduction of a chemically active compound covalently attached to the substrate surface prior to antibody addition. The antibody itself may also require the addition of a chemical activating group to achieve substrate bonding. These requirements are well known in the art. The substrate can be any medium capable of adsorbing or bonding to an antibody, for example a bead or nanoparticle (optionally chemically-activated), but is preferably of a planar conformation (optionally chemically-activated) such as a microtitre plate (as in Example 13 below) or a biochip. Microtitre plates commonly consist of 6, 24, 96, 384 or 1536 sample wells arranged in a 2:3 rectangular matrix. 96 well microtitre plates are commonly used in an ELISA. A biochip is a thin, wafer-like substrate with a planar surface which can be made of any suitable material such as glass or plastic but is preferably made of ceramic. The biochip is able to be chemically-activated prior to antibody bonding or is amenable to the passive adsorption of antibodies. The skilled person in biochip development for immunoassay application will recognize that a planar surface at high resolution e.g. if using a scanning electron microscope (SEM), is not perfectly 'flat' but will possess an uneven surface, the important aspect being that the 'approximately' planar surface is suitable for application. A microlayer coating of material can optionally be added to the planar surface of the substrate prior to antibody immobilisation. Either the upper surface or both surfaces of the substrate can be coated. In one embodiment other compound-specific or compound generic antibodies can also be incorporated onto the single substrate at discrete locations (so-called 'spatially addressable locations'), such as antibodies cross-reactive to the 2C-X and DOX sub-families, methamphetamine, amphetamine and/or MDMA. This would enable the proficient screening of biological, product and environmental samples by highlighting not only the presence of any phenethylamine based designer drugs in the sample, but also to which sub-family the phenethylamine(s) belong(s); this makes the subsequent mass spectrometric confirmatory step, if required, less analytically complex.

Methods and Results

General Methodology

Preparation of Haptens, Immunogens and Detecting Agents

Although haptens provide defined structural epitopes, they are not in themselves immunogenic and therefore need to be conjugated to carrier materials, which will elicit an immunogenic response when administered to a host animal. Appropriate carrier materials commonly contain poly(amino acid) segments and include polypeptides, proteins and protein fragments. Illustrative examples of useful carrier materials are bovine serum albumin (BSA), egg ovalbumin (OVA), bovine gamma globulin (BGG), bovine thyroglobulin (BTG), keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen. The haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof. Immunogen formation for the invention described herein involves conventional conjugation chemistry. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOFMS).

General Procedure for MALDI-TOF Analysis of Immunogens.

MALDI-TOF mass spectrometry can be performed using a Voyager STR Biospectrometry Research Station laser-desorption mass spectrometer coupled with delayed extraction. An aliquot of each sample to be analysed can be diluted in 0.1% aqueous trifluoroacetic acid (TFA) to create 1 mg/ml sample solutions. Aliquots (1 µl) can be analysed using a matrix of sinapinic acid and bovine serum albumin (Fluka) as an external calibrant.

Preparation of Antisera

In order to generate polyclonal antisera, 2 mg of an immunogen of the present invention is prepared in PBS, mixed at a ratio of 50% immunogen in PBS with 50% Freund's Complete adjuvant (Sigma, Product Number—F5881) and emulsified by repeatedly passing the mixture through a tip on the end of a 1 ml syringe, until it reaches the required semi-solid consistency. 1 ml of the mixture is then injected into a host animal, such as rabbit, sheep, mouse, guinea pig or horse. Sheep are the preferred host animal. Further injections (boosts) are administered on a monthly basis (1 mg of immunogen is prepared in PBS and mixed at a ratio of 50% immunogen in PBS with 50% of Freund's Incomplete Adjuvant, Sigma product Number—F5506) until the required titre is achieved. Serum is sampled for evaluation of the antibody titre.

Briefly, blood is collected by applying pressure to the exposed jugular vein and inserting a clean 14 gauge hypodermic needle to remove 500 ml of blood per sheep, under gravity. The blood is stored at 37° C. for a minimum of 1 hour before the clots are separated from the side of the centrifuge bottles using disposable 1 ml pipettes (ringing). The samples are stored at 4° C. overnight.

Samples are then centrifuged at 4200 rpm for 30 minutes at 4° C. The serum is poured off and centrifuged again, at 10,000 rpm for 15 minutes at 4° C., before being aliquoted and stored at <−20° C.

The Immunoglobulin (Ig) fraction is extracted from the antisera via caprylic acid/ammonium sulphate precipitation of immunoglobulin.

The antibody titre is evaluated by coating a microtitre plate (Thermo Fisher Scientific NUNC, 468667) with antibody (125 µl/well) in coating buffer (10 mM Tris pH 8.5) at 37° C. for 2 hours. The plate is then washed 4 times over 10 minutes with working strength TBST. 50 µl of sample/ standard (25I-NBOMe) is added to the appropriate wells in triplicate, followed by 75 µl of hapten-HRP conjugate and incubated at 25° C. for 1 hour. The plate is then washed and 125 µl of TMB (Randox Laboratories, 4380-15) added to each well and left at room temperature for 20 mins in the dark. The reaction is stopped using 125 µl of 0.2 M sulphuric acid. The absorbances are read at 450 nm with an ELISA microplate reader (BIO-TEK Instruments, Elx800) and the means calculated. Antibody sensitivity can then be determined.

When the optimal titre has been attained, the host animal is bled to yield a suitable volume of specific antiserum (overall this results in 20 bleeds in total, with approximately 200 ml of antiserum achieved per bleed). The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Various purification steps are available if required, including Immunoglobulin Precipitation (as described above), Antigen-specific affinity purification, Size-exclusion chromatography and Ion Exchange Chromatography.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunizing an animal, preferably a mammalian animal, by repeated administration of an immunogen. The serum from the immunized animal is collected when the antibody titre is sufficiently high. A detecting agent is added to a sample containing the target analyte and the raised antibodies, and the detecting agent and analyte compete for binding to the antibodies. The process may comprise fixing said serum antibodies to a backing substrate such as a polystyrene solid support or a ceramic chip. The antibodies can be polyclonal or monoclonal antibodies.

This can be carried out using an ELISA based format as described above for measuring antibody titre or as a Biochip based format. Details of how the antibodies are fixed to the Biochip are described in FitzGerald, S. P. et al, Clin. Chem. 51(7); 1165-1176; 2005. The signal emitted in the immunoassay is proportionate to the amount of detecting agent bound to the antibodies which in turn is inversely proportionate to the analyte concentration. The signal can be detected or quantified by comparison with a calibrator.

EXAMPLES (NUMBERS IN BOLD REFER TO STRUCTURES IN FIGS. 3 AND 4)

Example 1: Preparation of 1-(2,5-dimethoxyphenyl)nitroethene 2

A solution of 2,5-dimethoxybenzaldehyde (25 g, 0.15 mol), nitromethane (100 ml) and ammonium acetate (11.6 g, 0.15 mol) was heated at reflux for 5 hours and left stirring at room temperature overnight. The solvent was evaporated under vacuum, the residue was taken up in dichloromethane (500 ml) washed by water (2×100 ml), 3 M HCl solution (4×100 ml) and brine (100 ml). The organic layer was then dried over sodium sulphate, filtered and concentrated to dryness. The residue obtained was purified by column chromatography (Silica gel, 5-30% dichloromethane in hexane) to give 20.0 g of 1-(2,5-dimethoxyphenyl) nitroethene 2 as a light orange solid.

Example 2: Preparation of 2-(2,5-dimethoxyphenyl)ethylamine 3

To lithium aluminium hydride (10.32 g, 0.27 mol) was added anhydrous THF (300 ml). A solution of 1-(2,5-dimethoxyphenyl)nitroethene 2 (20.0 g, 0.956 mol) in THF (150 ml) was added drop-wise over a period of 45 min. The mixture was heated at reflux for 4 hours, after which thin-layer chromatography (TLC) analysis showed absence of starting material. After cooling at room temperature the reaction was quenched by the stepwise addition of 50% THF/$H_2O$ (10 ml), 15% NaOH solution and $H_2O$ (30 ml). The precipitate solids were removed by vacuum filtration, and the filtrate was reduced under vacuum to afford a yellow oil. The oil was dissolved in $Et_2O$ washed with $H_2O$ (2×100 ml) and then extracted into 1 M HCl (2×200 ml). The acidic extracts were washed with $Et_2O$ (2×75 ml) and then made strongly basic with 5 M NaOH. The basic solution was extracted with $Et_2O$ (3×150 ml). The ether extract was washed with water (2×100 ml), and brine (100 ml) dried over $Na_2SO_4$ and filtered. The filtrate was concentrated to dryness to provide 12.5 g of 2-(2,5-dimethoxyphenyl)ethylamine 3 as a clear oil.

Example 3: Preparation 2-(2,5-dimethoxy-4-nitrophenyl)ethylamine 4

To a cooled solution of 2-(2,5-dimethoxyphenyl)ethylamine 3 (12.0 g, 0.066 mol) in acetic acid (200 ml) was added nitric acid (40 ml) and the solution was stirred at 0° C. for 1 hour. The mixture was poured into a mixture of ice and water. The mixture was then made strongly alkaline with 6 M NaOH. The basic solution was extracted with a mixture of benzene/ether (1/1) (2×200 ml). The organic layers were washed by water (100 ml) and brine (100 ml), dried over $Na_2SO_4$ and filtered. The filtrate was concentrated to dryness under vacuum to give 11.2 g of 2-(2,5-dimethoxy-4-nitrophenyl)ethanamine 4 as a brown dark oil (crude) used in the next step without any further purification.

Example 4: Preparation of N-(2-Methoxybenzyl)-2-(2,5-dimethoxy-4-nitrophenyl)ethylamine 5 (25NO2-NBOMe)

To a solution of the crude 2-(2,5-dimethoxy-4-nitrophenyl)ethanamine 4 (4.52 g, 0.02 mol) in 1,2-dichloroethane (150 ml) at room temperature was added respectively 2-Methoxybenzaldehyde (4.0 g, 0.029 mol), TEA (4.8 ml, 0.029 mol) and Sodium triacetoxyborohydride (4.3 g, 0.02 mol). The mixture was then stirred at room temperature for 2 hours, after which TLC analysis showed absence of starting material 4. Water (200 ml) was added to the solution and the layers were separated and the aqueous layer was extracted by $CH_2Cl_2$ (2×150 ml). The combined organic layers were washed by water (150 ml) and brine (100 ml), dried over $Na_2SO_4$ and filtered. The filtrate was concentrated to dryness under vacuum. The residue obtained was purified by column chromatography (Silica gel, 5% MeOH in CH$_2$Cl$_2$ to give N-(2-Methoxybenzyl)-2-(2,5-dimethoxy-4-nitrophenyl)ethylamine 5 (4.1 g) as a foamy solid.

Example 5: Preparation of N-(2-Methoxybenzyl)-2-(4-Amino-2,5-dimethoxyphenyl)ethylamine (25NH2-NBOMe) (Hapten-1)

To a solution of N-(2-Methoxybenzyl)-2-(2,5-dimethoxy-4-nitrophenyl)ethylamine 5 (4.0 g, 0.012 mol) in methanol (100 ml) was added ammonium formate (3.071 g, 0.059 mol) and 5% Palladium on carbon (Pd/C) (1 g). The reaction mixture was stirred at room temperature for 2 hours, after which TLC analysis showed absence of starting material. The mixture was filtered on a Celite® plug and the filtrate was concentrated to dryness. The residue obtained was purified by column chromatography (Silica gel, 10% MeOH in CHCl$_3$) to give 2.8 g of white solid of N-(2-Methoxybenzyl)-2-(4-Amino-2,5-dimethoxyphenyl)ethylamine (25NH2-NBOMe) (Hapten-1).

Example 6: Preparation of N-(tert-Butoxycarbonyl)-N-(2-methoxybenzyl)-2-(2,5-dimethoxy-4-nitrophenyl)ethylamine 6

To a solution of N-(2-Methoxybenzyl)-2-(2,5-dimethoxy-4-nitrophenyl)ethylamine 5 (2.0 g, 0.006 mol) in dichloromethane (50 ml), was added TEA (1.87 ml, 0.012 mol) and catalytic amount of DMAP followed by di-tert-butyl dicarbonate (2.23 g, 0.012 mol) and the mixture was stirred at room temperature overnight. The solution was washed by water (40 ml) and brine (40 ml), dried over sodium sulphate and filtered. The filtrate was evaporated to dryness and the residue obtained was purified by column chromatography (Silica gel, 40% ethyl acetate in hexane) to give the N-(tert-Butoxycarbonyl)-N-(2-methoxybenzyl)-2-(2,5-dimethoxy-4-nitrophenyl)ethylamine 6 as yellow solid.

Example 7: Preparation of N-(tert-Butoxycarbonyl)-N-(2-methoxybenzyl)-2-(4-amino-2,5-dimethoxyphenyl)ethylamine 7

The N-(tert-Butoxycarbonyl)-N-(2-methoxybenzyl)-2-(4-amino-2,5-dimethoxyphenyl)ethylamine 7 was prepared by the same method as Example 5 from N-(tert-Butoxycarbonyl)-N-(2-methoxybenzyl)-2-(2,5-dimethoxy-4-nitrophenyl)ethylamine 6. The product 7 is obtained as yellow solid.

Example 8: Preparation of N-(tert-Butoxycarbonyl)-N-(2-methoxybenzyl)-2-(2,5-dimethoxy-4-succinamidophenyl)ethylamine 8

To a solution of N-(tert-Butoxycarbonyl)-N-(2-methoxybenzyl)-2-(4-amino-2,5-dimethoxyphenyl)ethylamine 7 (1.0 g, 0.0024 mol) in pyridine (10 ml) was added succinic anhydride (1.69 g, 0.016 mol) and the mixture was stirred at room temperature overnight. The pyridine was removed under vacuum. The residue obtained was purified by column chromatography (Silica gel, 10% MeOH in chloroform) to give 810 mg of N-(tert-Butoxycarbonyl)-N-(2-methoxybenzyl)-2-(2,5-dimethoxy-4-succinamidophenyl)ethylamine 8 as a white solid.

Example 9: Preparation of N-(2-methoxybenzyl)-2-(2,5-dimethoxy-4-succinamidophenyl)ethylamine TFA salt (Hapten-2)

To a cooled solution of N-(tert-Butoxycarbonyl)-N-(2-methoxybenzyl)-2-(2,5-dimethoxy-4-succinamidophenyl) ethylamine 8 (800 mg, 0.0015 mol) in dichloromethane (10 ml) at 0° C. was added trifluoroacetic acid (10 ml) and the mixture was left stirring at room temperature overnight. The solvent was removed under vacuum and then was triturated several times with Et$_2$O to give Hapten-2.

Example 10: Conjugation of N-(2-Methoxybenzyl)-2-(4-Amino-2,5-dimethoxyphenyl)ethylamine (25NH2-NBOMe) (Hapten-1) to BSA (Immunogen-1)

0.379 mL of N-(2-Methoxybenzyl)-2-(4-Amino-2,5-dimethoxyphenyl)ethylamine (25NH2-NBOMe) (Hapten-1) solution (3 mg/mL in Phosphate Buffered Saline, pH 7.2) was added to 2.5 mL of BSA solution (2 mg/mL in Phosphate Buffered Saline, pH 7.2), then equal volume of 2.0% Glutaraldehyde solution was added to the above mixture while stirring. The resulting solution was stirred at 15-25° C. for 1 hour. Sodium Borohydride was then added to final concentration at 10 mg/mL, and stirred for another 1 hour. Excess hapten was removed by dialysis at 2-8° C. against Phosphate Buffered Saline, pH 7.2.

MALDI results showed 31.7 molecule of (hapten-1) had been conjugated to one molecule of BSA.

Example 11: Conjugation of N-(2-Methoxybenzyl)-2-(4-Amino-2,5-dimethoxyphenyl)ethylamine (25NH2-NBOMe) (Hapten-1) to BTG (Immunogen-2)

7.583 mL of N-(2-Methoxybenzyl)-2-(4-Amino-2,5-dimethoxyphenyl)ethylamine (25NH2-NBOMe) (Hapten-1) solution (3 mg/mL in Phosphate Buffered Saline, pH 7.2) was added to 50 mL of carrier protein Bovine Thyroglobulin (BTG) (2 mg/mL in Phosphate Buffered Saline, pH 7.2), then equal volume of 2.0% Glutaraldehyde solution was added to the above mixture while stirring. The resulting solution was stirred at 15-25° C. for 1 hour. Sodium Borohydride was then added to final concentration at 10 mg/mL, and stirred for another 1 hour. Excess hapten was removed by dialysis at 2-8° C. against Phosphate Buffered Saline, pH 7.2.

Example 12: Conjugation of N-(2-methoxybenzyl)-2-(2,5-dimethoxy-4-succinamidophenyl)ethylamine (Hapten-2) to HRP N-(2-methoxybenzyl)-2-(2,5-dimethoxy-4-succinamidophenyl)ethylamine (Hapten-2) (3.0 mg) was dissolved in DMF (0.3 mL). and the resulting solution was added to N-Hydroxysuccinimide (1 mg), and pipet up and down until dissolved (this should take no longer than 30 seconds). The resulting solution was added to EDC hydrochloride (1.5 mg), and the mixture was incubated on the roller at room temperature for 2 hours. This solution was added drop-wise to a solution of HRP (20 mg) in 1.8 ml of Phosphate Buffered Saline, pH 8.0. The resulting solution was incubated on the roller at room temperature for 16-20 hours. Keep the solution darkened. Excess hapten was removed with PD-10 column (Pharmacia), pre-equilibrated with Phosphate Buffered Saline, pH 7.2, followed by dialysis at 2-8° C. against Phosphate Buffered Saline, pH 7.2.

Example 13: Development of an Immunoassay for NBOMe Based Compounds

IgG was extracted from the antisera using ammonium sulphate/caprylic acid precipitation and the purified antibody was immobilised on a 96 well ELISA plate at 5 µg/ml in 10 mM TRIS buffer, pH 8.5 overnight at 4° C. The assay is based on competition for binding sites of a polyclonal antibody between HRP tracer and 25I-NBOMe.HCL or potential cross-reactants. The plate was washed (×3) with TBST and the calibrator (25I-NBOMe.HCL) or potential cross reactants added (50 µl per well), followed by HRP tracer (75 µl/well) to the appropriate wells. The plates were then incubated for 60 minutes at 25° C. They were then subjected to 2 quick wash cycles using TBST, followed by 4×2 minute wash cycles. 125 µL of signal (TMB) was then added to each well for 20 mins at room temperature in the dark. The reaction was stopped by the addition of 125 µl of 0.2 M Sulphuric Acid per well and the plates read immediately at 450 nm. Calibration curves were generated and these were used to determine the sensitivity and specificity of the immunoassay for 25I-NBOMe-HCL and potential cross-reactants. The data are inputted to a computer program called 'KC Junior' (Biotek). It gives a 4 parameter fit curve and allows the calculation of concentrations between the standard runs. This program is used to calculate the $IC_{50}$ values by dividing the 0 ng/ml optical density (OD) value by 2 and obtaining the concentration value from the curve for this OD. The results of this study are presented in Tables 1-3, cross-reactivity being calculated according to the following formula:

$$\% \; CR = IC_{50 \; 25I\text{-}NBOMe.HCL} / IC_{50 \; CR} \times 100$$

Wherein % CR is the percentage cross-reactivity, $IC_{50 \; 25I\text{-}NBOMe \; HCL}$ is the concentration of 25I-NBOMe-HCL which causes 50% displacement of signal and $IC_{50 \; CR}$ is the concentration of potential cross-reactant that causes 50% displacement of signal.

The antibody (RS2708) used to generate the data in the tables below (each of the Tables) was raised from immunogen 2 (Example 11) and the HRP tracer was prepared as in Example 12. With the exception of the data in Table 3, all IC50 and cross reactivity data were generated using the immunoassay of Example 13. The data in Table 3 were generated using the same antibody (RS2708) raised from immunogen 2 (Example 11) and the HRP tracer (Example 12) but were generated on a different immunoassay platform.

TABLE 1

Antibody (RS2708) coated at 5 µg/ml, with HRP tracer at 1/64K

| Conc. | 25I-NBOMe•HCl | | |
|---|---|---|---|
| ng/ml | Ave OD | % CV | B/Bo |
| 0 | 2.258 | 1.0 | 100.0 |
| 0.03125 | 2.036 | 1.6 | 90.2 |
| 0.0625 | 1.811 | 0.8 | 80.2 |
| 0.125 | 1.383 | 0.5 | 61.3 |
| 0.25 | 0.754 | 1.7 | 33.4 |
| 0.5 | 0.331 | 2.1 | 14.7 |
| 1 | 0.172 | 3.3 | 7.6 |
| 2 | 0.119 | 2.4 | 5.3 |
| $IC_{50}$ | 0.164 ng/ml | | |

TABLE 2

Cross reactivity with NBOMe family compounds: Antibody (RS2708) coated at 5 µg/ml, with HRP tracer at 1/64K.

| Standard | $IC_{50}$ (ng/ml) | % Cross-reactivity |
|---|---|---|
| 25I-NBOMe•HCl | 0.164 | 100 |
| 25P-NBOMe•HCl | 0.147 | 111.6 |
| Mescaline-NBOMe•HCl | 0.1 | 164 |
| 25B-NBOMe•HCl | 0.138 | 118.8 |
| 25D-NBOMe•HCl | 0.104 | 157.7 |
| 25E-NBOMe•HCl | 0.13 | 126.2 |
| 25N-NBOMe•HCl | 0.142 | 115.5 |
| 25T2-NBOMe•HCl | 0.136 | 120.6 |
| 25T4-NBOMe•HCl | 0.139 | 118 |
| 25T7-NBOMe•HCl | 0.139 | 118 |
| 25H-NBOMe•HCl | 0.096 | 170.8 |
| 25N-NBOH | 0.615 | 26.7 |
| 25(NH2)-NBOH | 0.887 | 18.5 |

Cross-Reactivity

To test the cross-reactivity of the antibodies against a range of compounds, they were first immobilized on a biochip platform (9 mm×9 mm) (Randox Laboratories Ltd.), which was the vessel for the immunoreactions. The semi-automated bench top analyser Evidence Investigator was used (EV3602, Randox Laboratories Ltd., Crumlin, UK, patents—EP98307706, EP98307732, EP0902394, EP1227311, EP1434995 and EP1354623). The assay principle is based on competition for binding sites of the polyclonal antibodies (RS2708 raised against the immunogen of Example 11) between free antigen (cross-reactants) and labelled conjugate (Hapten 2-HRP, prepared as in Example 12). Assay diluent (155 µl), calibrator/25I-NBOMe or potential cross-reactant (25 µl) followed by Hapten 2-HRP conjugate (120 µl) were added to the appropriate biochip. The biochips were then incubated for 30 minutes at 30° C. on a thermo-shaker set at 370 rpm. The biochips were then subjected to 2 quick wash cycles using the wash buffer provided, followed by 4×2 minute wash cycles. 250 µl of signal (1:1 luminol+peroxide, v/v) was then added to each biochip, and after 2 minutes the biochip carrier was imaged in the Evidence Investigator analyser. The system incorporates dedicated software to automatically process, report and archive the data generated (details can be found in FitzGerald, S. P. et al, *Clin. Chem.* 51(7); 1165-1176; 2005). Table 3 shows the compounds tested, all of which elicited a negative response (cross-reactivity <1% compared to 25I-NBOMe) to the antibodies of the present invention.

TABLE 3

| Compound | NEG RESPONSE Tested at Conc (ng/ml) |
|---|---|
| Mephedrone | 16 |
| mcPP | 16 |
| N-Ethylcathinone | 16 |
| MDPBP | 16 |
| Methylone HCl | 16 |
| Methcathinone | 16 |
| 3-Fluoromethcathinone | 16 |
| Flephedrone HCl | 16 |
| BZP | 16 |
| MDPPP HCl | 16 |
| MDMA | 16 |
| DOB | 16 |
| Fenfluramine | 16 |
| Phentermine | 16 |

TABLE 3-continued

| Compound | NEG RESPONSE Tested at Conc (ng/ml) |
|---|---|
| 2CT-7 HCl | 16 |
| 2C-I | 16 |
| PMMA HCl | 16 |
| 5-IT | 16 |
| 6-APB | 16 |
| 5-MAPB | 16 |
| Ethylone HCl | 16 |
| TFMPP | 16 |
| S(−)Methcathinone | 16 |
| 5-APB | 16 |
| PMA HCl | 16 |
| Methylethcathinone HCl | 16 |
| R(+)Methcathinone HCl | 16 |
| (±) MBDB HCl | 16 |
| 2C-B | 16 |
| Butylone HCl | 16 |
| Methadrone HCl | 16 |
| DOET | 16 |
| 2C-E HCl | 16 |
| Bromo-Dragonfly | 16 |
| (±) MDA | 16 |
| MDPV | 16 |
| DOM | 16 |
| 5-APDB | 16 |
| D-Amphetamine | 16 |
| TMA | 16 |
| Buphedrone | 16 |
| S(+)Methamphetamine | 16 |
| (±) Amphetamine | 16 |
| Methyethcathinone HCl | 16 |
| Methylphenidate | 16 |
| Ephedrine | 16 |
| Pseudoephedrine | 16 |
| RH-34 | 16 |
| N-Ethylamphetamine | 16 |
| (±) Cathinone HCl | 16 |

Antibodies of the present invention bind to an epitope of Structure (Y)

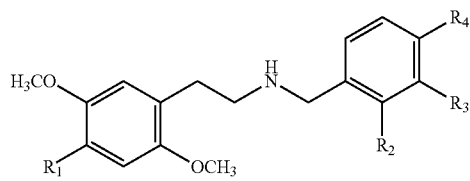

in which $R^1$ is selected from a halogen, hydrogen, hydroxyl, $C_{1-3}$ alkyl, $C_{1-3}$ thioalkyl, $C_{1-3}$ alkoxy, perfluoromethyl and nitro; $R^2$, $R^3$ and $R^4$ are independently selected from H or a $C_{1-3}$ alkoxy; or $R^2$ and $R^3$ together form —O—CH$_2$—O—.

Optionally, antibodies of the present invention bind to an epitope of Structure (Y'),

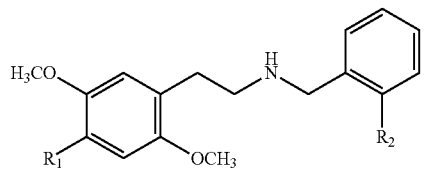

in which $R^1$ is selected from a halogen, hydrogen, hydroxyl, $C_{1-3}$ alkyl, $C_{1-3}$ thioalkyl, $C_{1-3}$ alkoxy, perfluoromethyl and nitro; and $R^2$ is selected from H or a $C_{1-3}$ alkoxy.

Optionally, antibodies of the present invention bind to an epitope of Structure (Y'), in which $R^1$ is selected from a halogen, hydrogen, hydroxyl, $C_{1-3}$ alkyl, $C_{1-3}$ thioalkyl, $C_{1-3}$ alkoxy, perfluoromethyl and nitro; and $R^2$ is selected from H and methoxy.

Further optionally, antibodies of the present invention bind to an epitope of Structure (Y'), in which $R^1$ is selected from a halogen, hydrogen, $C_{1-3}$ alkyl, $C_{1-3}$ thioalkyl, $C_{1-3}$ alkoxy, and nitro; and $R^2$ is methoxy.

Still further optionally, antibodies of the present invention bind to an epitope of Structure (Y'), in which $R^1$ is selected from a halogen (optionally selected from I, Br and Cl), hydrogen, $C_{1-3}$ alkyl (optionally selected from methyl, ethyl and propyl), $C_{1-3}$ thioalkyl (optionally selected from propylthio and isopropylthio), $C_{1-3}$ alkoxy (optionally methoxy), and nitro; and $R^2$ is methoxy.

The cross reactivity data of Table 2 show that, when compared to 100% for 25I-NBOMe.HCl, substances sharing the epitope of Structure (Y) or optionally (Y') show a cross reactivity of 75 to 200%. Antibodies of the present invention, therefore, can be utilised to detect or determine phenethylamines of the NBOMe sub-family and sharing the epitope of Structure (Y) or optionally (Y').

The cross reactivity data of Table 2 also show that, when other substances are assessed that do not share the epitope of Structure (Y) or optionally (Y') (25N-NBOH and 25(NH2)-NBOH), such substances show, when compared to 100% for 25I-NBOMe.HCl, a cross reactivity of less than 35%, optionally, less than 30%. In addition, the cross reactivity data of Table 2 show that, when the cross reactivity of 25N-NBOH is compared with 25N-NBOMe, the only difference being $R_2$ substituent, there is a dramatic difference in cross reactivity confirming the importance of the $R_2$ substituent being methoxy.

The cross reactivity data of Tables 2 and 3 also show that, when the cross reactivity of 25H-NBOMe is compared with RH-34 (each retains the $R_2$ substituent (methoxy)), there is, again, a dramatic difference in cross reactivity confirming that the identity of the $R_1$ dimethoxy phenyl group is important (in RH-34, this is replaced with a quinazoline-2,4-dione group).

As stated in the introduction above, the 2C-X compounds are substituted 2,5-dimethoxyphenethylamines in which, referring to Structure (X), $R^3$ and $R^6$ are methoxy, $R^4$ is not hydrogen and $R^N$, $R^\alpha$ and $R^\beta$ is hydrogen:

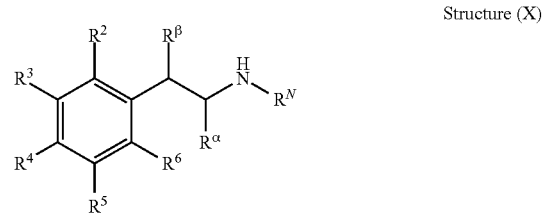

Structure (X)

Similarly, DOB is also a substituted 2,5-dimethoxyphenethylamine in which $R^3$ and $R^6$ are methoxy, $R^4$ is bromo, $R^N$ and $R^\beta$ is hydrogen and $R^\alpha$ is methyl. In contrast, in the NBOMe compounds, $R^N$ is an optionally substituted benzyl derivative.

The 2C-X compounds and DOB share, in Structure (X), $R^3$ and $R^6$ are methoxy, $R^4$ is not hydrogen and $R^2$, $R^5$, $R^N$ and $R^\beta$ are each hydrogen. The NBOMe compounds differ from the 2C-X compounds and DOB mainly but not exclusively by the definition of $R^N$ in Structure (X).

TABLE 4

Cross reactivity of the NBOMe ELISA with compounds from the 2C-X and DOX sub-families of phenethylamines: Antibody (RS2708) coated at 5 μg/ml, with HRP tracer at 1/64K. Samples @ 100 ng/ml

| Compound | Ave OD | % CV | B/Bo | IC$_{50}$ | % CR |
|---|---|---|---|---|---|
| 2C-I | 2.003 | 3.0 | 88.8 | >100 | <0.16 |
| 2C-E | 2.082 | 0.8 | 92.2 | >100 | <0.16 |
| DOB | 2.072 | 2.4 | 91.8 | >100 | <0.16 |
| 2C-B | 2.029 | 1.0 | 89.9 | >100 | <0.16 |

DOB is 2,5-Dimethoxy-4-bromoamphetamine and 2C-B, 2C-E and 2C-I are depicted below

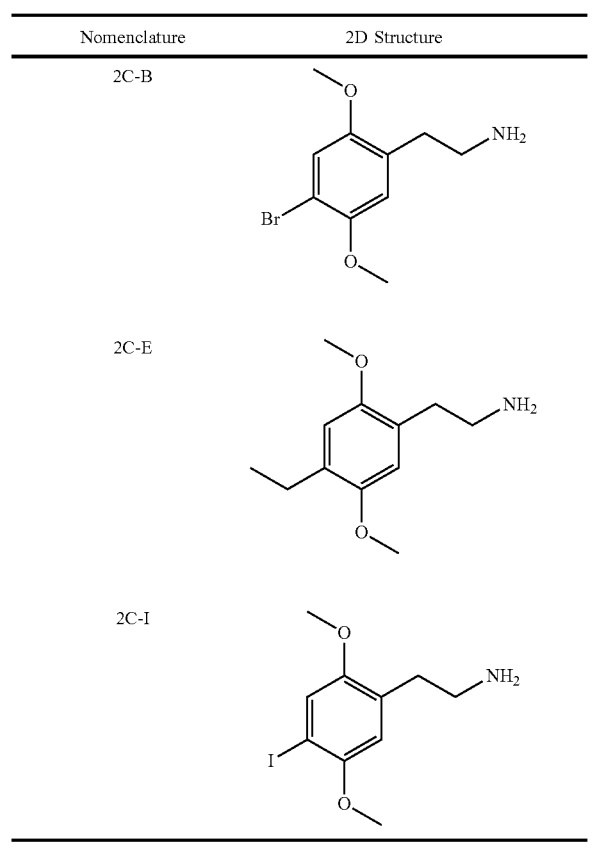

| Nomenclature | 2D Structure |
|---|---|
| 2C-B | |
| 2C-E | |
| 2C-I | |

The cross reactivity data of Table 4 show a % cross reactivity, optionally when measured according to Example 13, when compared to 100% for 25I-NBOMe.HCl, of less than 5%, optionally, less than 4% or 3%, further optionally less than 2% or 1% for substances of Structure (X) in which R$^3$ and R$^6$ are methoxy, R$^4$ is not hydrogen and R$^2$, R$^5$, R$^N$ and R$^\beta$ are each hydrogen.

The cross reactivity data of Table 4 show a % cross reactivity, optionally when measured according to Example 13, when compared to 100% for 25I-NBOMe.HCl, of less than 5%, optionally, less than 4% or 3%, further optionally less than 2% or 1% for substances of Structure (X) selected from one or more of DOB (2,5-Dimethoxy-4-bromoamphetamine), 2C-B, 2C-E and 2C-I.

The Table 4 data show that the antibodies of the present invention bind to an epitope of Structure (Y) or optionally (Y'). The substances from the 2C-X and DOX sub-families of Structure (X) lack the substituted benzyl ring of Structure (Y) or optionally (Y'). The dramatically lower cross reactivity demonstrates that the antibodies of the present invention are also binding to the substituted benzyl ring of Structure (Y) or optionally (Y'), when measured according to Example 13.

We claim:

1. An antibody which binds to epitope of Structure (Y)

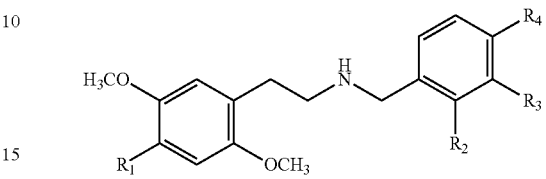

in which R$^1$ is selected from the group consisting on a halogen, hydrogen, hydroxyl, C$_{1-3}$ alkyl, C$_{1-3}$ thioalkyl, C$_{1-3}$ alkoxy, perfluoromethyl and nitro; R$^3$ and R$^4$ are H and R$^2$ is methoxy;

wherein the antibody shows a cross-reactivity of 75 to 200% to the epitope of the Structure (Y) and a cross-reactivity of less than 5% to 2-(4-Iodo-2,5-dimethoxyphenyl) ethanamine (2C-I), 2-(4-ethyl-2,5-dimethoxyphenyl)ethanamine (2C-E), 2,5-dimethoxy-4-bromoamphetamine (DOB) and 2-(4-bromo-dimethoxyphenyl)ethanamine (2C-B); and wherein the cross-reactivity is relative to 100% cross-reactivity of the antibody to 2-(4-Iodo-2,5-dimethoxyphenyl)-N-[(2-methoxyphenyl)methyl] ethanamine (25I-NB)Me).

2. The antibody of claim 1, which binds to an epitope of at least one of 2-(4-Iodo-2,5-dimethoxyphenyl)-N-[(2-methoxyphenyl)methyl] ethanamine (25I-NBOMe), 2-(2,5 dimethoxy-4-propylphenyl)-N-(2-methoxybenzyl)ethanamine (25P-NBOMe), Mescaline-[(2-methoxvpheny)methyl]ethanamine (Mescaline-NBOMe), 2-(4-Bromo-2,5-dimethoxyphenyl)-N-[(2-methoxyphenyl)methyl] ethanamine (25B-NBOMe), 2-(2,5-Dimethoxy-4-methyl-phenyl)-N-[(2-methoxyphenyl)methyl]ethanamine (25D-NBOMe), 2-(4-ethyl-2,5-dimethoxyphenyl)-N-(2-methoxybenzyl)ethanamine (25E-NBOMe), 2-(2,5-dimethoxyphenyl)-N-(2-methoxybenzyl)ethanamine (25H-NBOMe), 2-(2,5-dimethoxy-4-nitrophenyl)-N-(2-methoxybenzyl)ethanamine (25N-NBOMe), 2-[2,5-dimethoxy-4-(-methylsulfanyl)phenyl]-N-(2-methoxybenzyl)ethanamine (25T2-NBOMe), 2-[(4-isopropylsulfanyl)-2,5-dimethoxyphenyl]-N-(2-methoxybenzyl)ethanamine (25T4-NBOMe) and 2-[2,5-dimethoxy-4(propylsulfanyl)phenyl]-N-(2-methoxybenzyl) ethanamine (25T7-NBOMe).

3. The antibody of claim 1 with an antibody sensitivity of IC50 of 0.2 ng/ml or less for 2-(4-iodo-2,5-dimethoxyphenyl)-N-[(2-methoxyphenyl)methyl] ethanamine (25I-NBOMe), 2-(2,5 dimethoxy-4-propylphenyl)-N-(2-methoxybenzyl)ethanamine (25P-NBOMe), mescaline-2-methoxyphenyl)methyl]ethanamine (mescaline-NBOMe), 2 (4-bromo-2,5-dimethoxyphenyl)-N-[(2-methoxyphenyl) methyl]ethanamine (25B-NBOMe), dimethoxy-4-methyl-phenyl)-N-[(2-methoxyphenyl)methyl]ethanamine (25D-NBOMe), 2-(4-ethyl-2,5-dimethoxyphenyl)-N-(2-methoxybenzyl)ethanamine (25E-NBOMe) 2-(2,5-dimethoxyphenyl)-N-(2-methoxybenzyl)ethanamine (25H-

NBOMe), 2-(2,5-dimethoxy-4-nitrophenyl)-N-(2-methoxybenzyl)ethanamine (25N-NBOMe), 2-[2,5-dimethoxy-4-(methylsulfanyl)phenyl]-N-(2-methoxybenzyl)ethanamine (25T2-NBOMe), 2-[4-isopropylsulfanyl)-2,5-dimethoxyphenyl]-N-(2-methoxybenzyl)ethanamine (25T4-NBOMe) and 2-[2,5-dimethoxy-4(propylsulfanyl)phenyl]-N-(2-methoxybenzyl)ethanamine (25T7-NBOMe).

4. The antibody of claim 1 further characterized by being derived from an immunogen of structure II

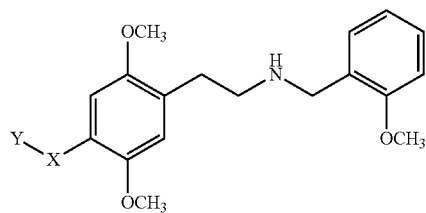

Structure (II)

wherein X is a cross-linking group and Y is an antigenicity-conferring carrier.

5. The antibody of claim 4 wherein X is -(A)-(B)n-, where A is O, S or N and B is a $C_{1-6}$ substituted or unsubstituted straight chain alkylene or arylene moiety and n is either 0 or 1.

6. The antibody of claim 1, which binds to an epitope of at least one of 25I-NBOMe, 25P-NBOMe, Mescaline-NBOMe, 25B-NBOMe, 25D-NBOMe, 25E-NBOMe, 25H-NBOMe, 25N-NBOMe, 25T2-NBOMe, 25T4-NBOMe and 25T7-NBOMe.

7. The antibody of claim 1 with an IC50 of 0.2 ng/ml or less for 25I-NBOMe, 25P-NBOMe, Mescaline-NBOMe, 25B-NBOMe, 25D-NBOMe, 25E-NBOMe 25H-NBOMe, 25N-NBOMe, 25T2-NBOMe, 25T4-NBOMe and 25T7-NBOMe.

8. The antibody of claim 1 further characterized by being derived from an immunogen of structure II

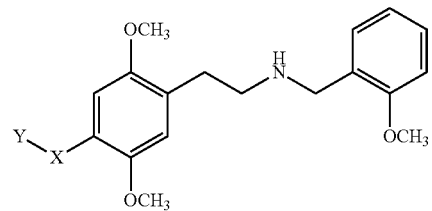

Structure (II)

wherein X is a cross-linking group and Y is an antigenicity-conferring carrier.

9. A substrate comprising an antibody of one of claim 1, 2, 3, 4, 5, 6, 7 or 8, wherein optionally the substrate is either a microtitre plate or a biochip.

10. A kit comprising an antibody according to one of claim 1, 2, 3, 4, 5, 6, 7 or 8, and optionally one or more detecting agents of structure III

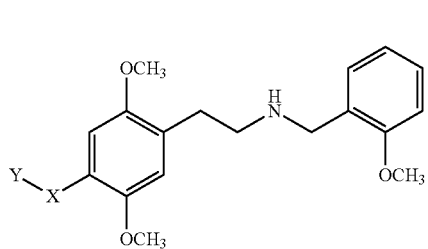

Structure (III)

in which X is a cross-linking group and Y is a labelling agent which is detectable; and optionally wherein X is -(A)-(B)$_{n1}$—, where A is O, S or N and B is a $C_{1-6}$ substituted or unsubstituted straight chain alkylene or arylene moiety and $_{n1}$ is either 0 or 1; wherein, optionally, X is -(A)-(B)$_{n1}$—, where A is O, S or N and B is a $C_{1-6}$ substituted or unsubstituted straight chain alkylene terminating, before conjugation with the labelling agent, with a terminal reactive group and $_{n1}$ is either 0 or 1; wherein, further optionally, X is -(A)-(B)$_{n1}$—, where A is N and B is a $C_{1-6}$ substituted or unsubstituted straight chain alkylene terminating, before conjugation with the labelling agent, with a terminal reactive group and $_{n1}$ is either 0 or 1.

* * * * *